US00PP28931P3

(12) United States Plant Patent
Kallsen et al.

(10) Patent No.: US PP28,931 P3
(45) Date of Patent: Feb. 6, 2018

(54) MALE PISTACHIO TREE NAMED 'TEJON'

(50) Latin Name: ***Pistacia vera* L.**
Varietal Denomination: Tejon

(71) Applicant: The Regents of the University of California, Oakland, CA (US)

(72) Inventors: Craig E. Kallsen, Davis, CA (US); Dan E. Parfitt, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/999,157

(22) Filed: Apr. 4, 2016

(65) Prior Publication Data

US 2017/0099754 P1 Apr. 6, 2017

Related U.S. Application Data

(60) Provisional application No. 62/236,801, filed on Oct. 2, 2015.

(51) Int. Cl.
*A01H 5/08* (2006.01)

(52) U.S. Cl.
USPC ..... Plt./152

(58) Field of Classification Search
USPC ..... Plt./152
See application file for complete search history.

(56) References Cited

PUBLICATIONS

Hickey (1973). "Classification of the Architecture of Dicotyledonous Leaves," American Journal of Botany, 60(1): 17-33.
Hormaza et al. (1996). "Pistillate and staminate flower development in dioecious *Pistacia vera* (Anacardiaceae)," American Journal of Botany, 83(6): 759-766.
The Apr. 1, 2012 Test Agreement for Trees (No. 2012-5014) between Gary Stiefvater and The Regents of The University of California, 6 pages.
The Jun. 1, 2012 Test Agreement for Trees (No. 2015-5007) between Aldo Antongiovanni and sons and The Regents of The University of California, 7 pages.
The Jun. 1, 2014 Test Agreement for Trees and Rootstocks (No. 2014-5014) between Paramount Farming Company, LLC and The Regents of the University of California, 7 pages.
The Aug. 1, 2014 Test Agreement for Trees (No. 2014-5015) between Mid Valley Ranch, LLC and The Regents of The University of California, 8 pages.

*Primary Examiner* — Susan McCormick Ewoldt
(74) *Attorney, Agent, or Firm* — Morrison & Foerster LLP

(57) ABSTRACT

A new male pistachio tree (*Pistacia vera* L.) designated as 'Tejon', particularly characterized by very early to early flowering time, is provided. The male pistachio tree 'Tejon' is further characterized by a large number of flowers. In addition, 'Tejon' is characterized by the production of large quantities of durable pollen with a high germination ratio.

9 Drawing Sheets

Latin name: Botanical/commercial classification: *Pistacia vera* L.

Varietal denomination: The varietal denomination of the claimed pistachio variety is 'Tejon'.

BACKGROUND OF THE INVENTION

An objective of pistachio breeding programs is to develop new varieties that can be harvested at unique times relative to other pistachio varieties. The female pistachio variety 'Kerman' (not patented) is the main later-season pistachio cultivar grown in California and in other parts of the world, but other female pistachio varieties are also grown, such as 'Golden Hills' (U.S. Plant Pat. No. 17,158). A major problem for pistachio growers that has developed with the rapid increase in pistachio plantings in California, for example, is the availability of harvest equipment/contractors and processing capacity, since most of the existing crop ('Kerman') matures at about the same time. 'Golden Hills' has become a popular alternative to 'Kerman' because it can be harvested before 'Kerman', and other early-flowering female pistachio varieties have also been developed (e.g. 'Gumdrop', U.S. application Ser. No. 14/999,158). The development of multiple female pistachio varieties that flower in a time series is advantageous because this will allow these varieties to be harvested in a time series, which will increase the availability of pistachio harvesting equipment and processing capacity.

Developing a harvest date series is an optimal way to use existing harvest equipment and processing plant resources. Without staggered harvest dates, the pistachio industry will have to develop significantly increased (e.g. 2×) harvesting capability (which is now provided by custom harvestors) and find investors willing to fund new processing plants (which are only used for a few weeks per year). Failure to develop either these facilities or a harvest date series will expose the industry to significant risk from aflatoxin contamination in the crop due to extended pre-processing times.

In order to develop a successful harvest date series, male pistachio varieties whose flowering times sufficiently overlap with that of appropriate female pistachio varieties will need to be available. Female pistachio varieties require a properly synchronized male pollinizer to ensure fruit set, but even the earliest-flowering male pistachio variety being used in the industry ('Randy', U.S. Plant Pat. No. 18,262) is unable to effectively pollinate early-flowering female pistachio varieties (e.g. 'Gumdrop') due to late flowering or poor flowering overlap. Male pistachio varieties that exhibit better flowering synchrony and overlap better with early-flowering female pistachio varieties than 'Randy' will aid in developing a successful harvest date series.

Further, poor synchrony between male and female pistachio trees is increased during low-chill years, and results in insufficient pollen during bloom. To address this, the pistachio industry is moving back to the older practice of including earlier-blooming males in orchard designs. For example, growers are commonly adding 'Randy' to new 'Kerman' plantings, or grafting 'Randy' onto 'Peters' (not patented) trees in existing plantings. It would be advantageous to have additional male varieties that can pollinize even earlier than 'Randy' to provide early pollen in low-chill years.

Thus, there exists a need for improved male pistachio varieties with earlier flowering dates than the present industry standards. The present male pistachio variety 'Tejon' described herein is a product of the breeding efforts to produce improved pistachio varieties.

SUMMARY OF THE INVENTION

The present invention relates to a new and distinct pistachio cultivar (*Pistacia vera* L.) which has been denominated as 'Tejon', and more particularly as a male pistachio variety which exhibits earlier flowering dates compared to the industry standard 'Randy' cultivar.

'Tejon' produces a large number of flowers and large quantities of durable pollen with a high germination ratio. 'Tejon' is a very early flowering male pistachio variety, flowering 6 to 10 days earlier than the male pistachio variety 'Randy'. The flowering time of 'Tejon' also overlaps with the bloom period of the female pistachio variety 'Gumdrop'. 'Gumdrop' flowers much earlier than currently planted female pistachio cultivars, thus 'Tejon' should serve the pistachio industry well as a suitable pollinizer variety for 'Gumdrop'. It is believed that 'Tejon' will provide the needed pollination overlap with 'Gumdrop' and other early-flowering female pistachio varieties across multiple years and with differing winter chilling seasons. 'Tejon' may also serve as a significant pollinizer across diverse climates including, for example, California, New Mexico, Arizona, and other regions of pistachio production, especially those areas that exhibit lower winter chilling. Pistachio growers and/or nursery companies producing budded pistachio cultivars may be consumers of 'Tejon', as would growers producing nuts (who would probably obtain budwood or budded trees from a nursery source). 'Tejon' may also be included as a male pollinizer variety in plantings of female pistachio varieties such as e.g. 'Golden Hills' and 'Lost Hills' (U.S. Plant Pat. No. 17,701) to provide additional early pollen in low-chill years, or to supplement 'Randy' pollen.

'Tejon' was originally identified as an open-pollinated offspring of female pistachio seedling selection 'B4-19' (not patented), the open-pollination having taken place in a pistachio breeding program test plot near Bakersfield, Calif. during Year 0. The initial seedling was originally designated as selection 'N-48'. During the open-pollination that produced 'N-48', three male pistachio varieties were located near the female selection 'B4-19': male varieties 'Peters', 'Randy', and 'B6-6' (not patented). Since both 'Peters' and 'B6-6' are very late flowering males ('B6-6' is later than 'Peters'), it is believed that 'Tejon' was the result of a cross between the 'B4-19' female (a very early flowering selection) and 'Randy' (the early flowering male variety at that location). The female selection 'B4-19' is a cloned seedling from a cross between a *Pistacia vera* L. female ('2-35') and an unknown *Pistacia vera* L. male, and the male variety 'Randy' is the cloned progeny from a cross of the female selection '2-35' (not patented) and the male selection 'ES#3' (not patented).

The original seedling 'N-48' was collected and germinated at an extension office in Bakersfield, Calif., USA in February of Year 1, and planted and grown in a small test plot at this location in Year 1. 'N-48' was initially asexually reproduced (budwood grafted onto rootstocks) and established in replicated advanced selection trials at a Buttonwillow, Calif., USA test plot and a test plot designated as the Jasmine trial in Kern County, Calif., USA in Year 12. The rootstock used in the Jasmine trial was 'UCB-1' (not patented). 'N-48' was not an original entry in the Buttonwillow and Jasmine trials. After the first season, when initial flowering was observed at the Buttonwillow trial, several of the female selections in that trial (e.g. 'Gumdrop') bloomed earlier (compared to the timing of the male variety 'Randy' bloom) when grafted on rootstocks than when on their own roots. Because these female selections need a pollinizer with a bloom period that overlaps with their own, 'N-48' was grafted into the trial in Year 12. 'N-48' was chosen because this selection had a long bloom period and was at full bloom about four days earlier than 'Randy'. 'N-48' also rated a 4 (1=low, 4=high) on a flower density scale, and each inflorescence produced copious pollen with good germination. The precociousness of 'N-48', initially observed in the seedling selection trials, was further demonstrated by the observation that it bloomed only two years after it was grafted onto an existing tree in the Buttonwillow trial. 'N-48' is at full bloom at least two weeks before the female variety 'Kerman', with little or no overlap with 'Kerman'.

'N-48' is also present as a single tree grafted onto rootstock in a pistachio germplasm repository located in Bakersfield, Calif., USA. 'N-48' was also grafted onto 'PG1' ('Pioneer Gold 1', not patented) rootstock in another trial, the Bakersfield trial, in Year 8.

Selection 'N-48' was chosen as a candidate for release under the variety name 'Tejon', and will be useful as a male pollinizer of early-flowering female pistachio varieties. It is believed that use of earlier flowering cultivars will become increasingly common as climate change continues to reduce average chilling periods. The variety 'Tejon' has been found to be stable and reproduce true to type through successive asexual propagations.

DETAILED BOTANICAL DESCRIPTION

Figure 1:
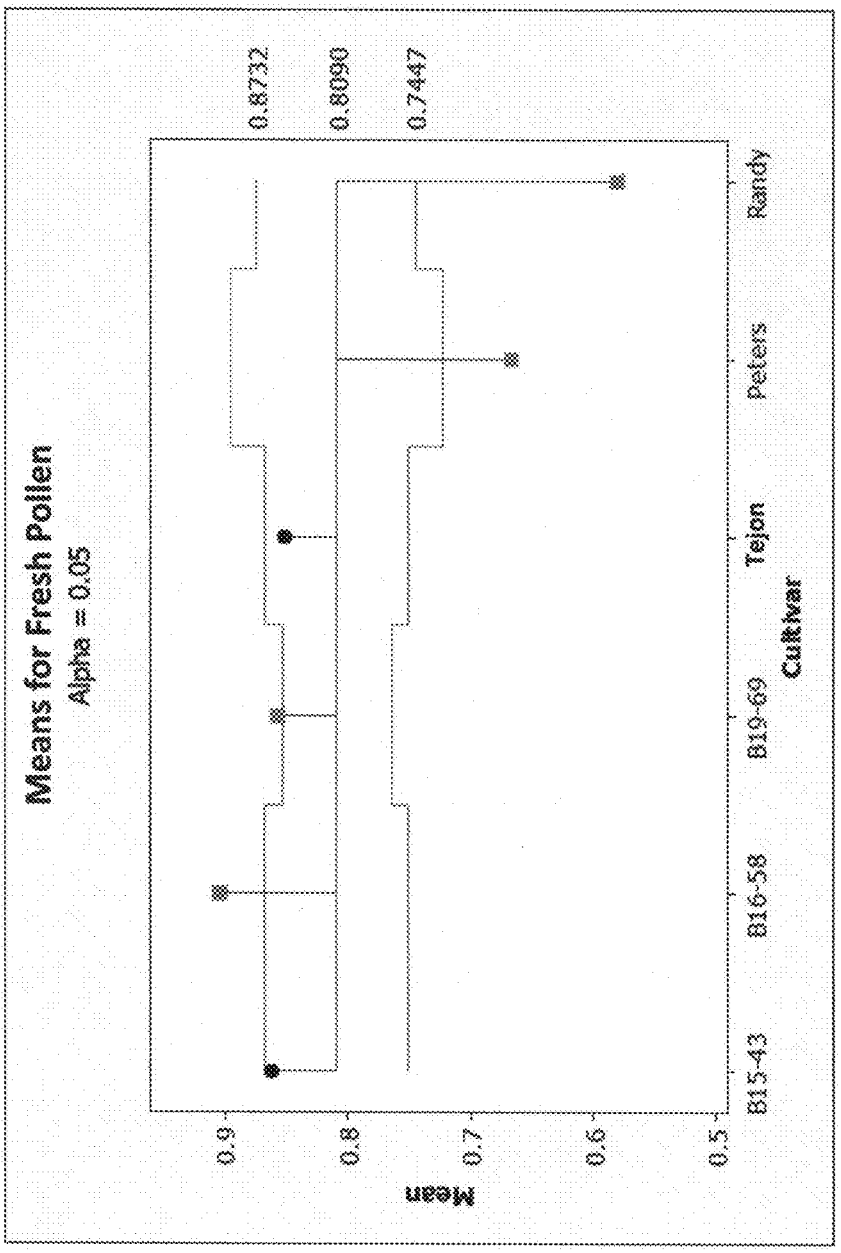
FIG. 1 illustrates the mean germination ratio of freshly-collected pollen for 7-year-old 'Tejon' trees and other male pistachio varieties in Year 15. Shown is the analysis of means (MiniTab 17) with 5% SD, where a value of 1.0=100%.

The following is a detailed botanical description of the new male pistachio cultivar designated as 'Tejon', including the key differentiating characteristics of this variety and comparisons of certain characteristics of 'Tejon' to other pistachio varieties. Unless otherwise indicated, evaluation data was taken from 2- to 5-year-old trees. As described below, pollen data was obtained from 7-year-old trees. Color descriptions are based on the color standards presented in R.H.S. Colour Chart of The Royal Horticultural Society of London (R.H.S.) (1st edition, 1966).

Summary of Trials:

'N-48' has been evaluated in two randomized, replicated advanced selection trials: the Buttonwillow trial and the Jasmine trial, as described below.

The Buttonwillow trial consists of nine different female selections. Each female selection is in a plot consisting of 6 trees of that selection. Each female plot is replicated three times, once in each of three randomized blocks providing a total of 18 trees of each female selection. Each block is separated by a male row containing replicated males of 'Peters', 'Randy', and 'Tejon'. There are two of these replicated male rows within the trial. The trial is surrounded by typical male rows containing 'Peters'. Flowering/bloom data presented herein for 'Tejon' and comparative varieties were obtained from the Buttonwillow trial.

The Jasmine trial contains additional different female and male varieties as compared to the Buttonwillow trial. The Jasmine trial is also randomized and replicated in a similar fashion as the Buttonwillow trial. 'Tejon' shows precociousness in this trial as well, and the 'Tejon' trees (budded in Year 12) have caught up to the other male varieties with respect to flowering, and are covered with flower buds.

'Tejon' has also been evaluated in Bakersfield, Calif., USA and another trial location near Famoso, Calif. Pollen data presented herein for 'Tejon' was obtained from plants at this location in Year 15 (7-year-old trees).

Tree Size:

Tree height was about 2-3 meters in Year 17 (5-year-old trees). Both 'Randy' and 'Peters' were planted in this plot for comparison. All cultivars were similar in size (not significantly different). Trunk cross sectional area measurements are not available as the 'Tejon' male cultivar where tree size data was taken was grafted on the rootstock as branches rather than budded directly on the main stem of the rootstock, as was done for 'Randy' and 'Peters'. Therefore trunk measurements were not considered to be meaningful.

Bark:

The bark of 'Tejon' trees is grey (202C-D). Photographs were taken of the trunks of two trees for each of the 'Tejon', 'Peters', and 'Randy' varieties for the purpose of evaluating differences in trunk lenticel density in Year 17 at the Jasmine trial (5-year-old 'Tejon' trees). 5 cm and 10 cm templates were used for the photographs. Counts were normalized to counts/cm. 7 to 10 evaluations were done per cultivar with count values of circa 50 to 250 counts per observation. ANOVAs were computed with MiniTab 17. Significant differences were found (p=0.029). 'Tejon' had fewer lenticels than 'Peters' or 'Randy'. Like the male 'Famoso' (U.S. application Ser. No. 14/999,156), lenticels were very irregular in arrangement with fewer compound lenticels. That is unlike most pistachios, in which lenticels are arranged in horizontal rows. The means table for all three cultivars is shown in Table 1 (unit is number of lenticels/$cm^2$).

TABLE 1

Mean number of lenticels/$cm^2$

| Cultivar | Mean | SE Mean | StDev | p value |
|---|---|---|---|---|
| Tejon | 10.53 | 0.97 | 2.57 | 0.029 |
| Randy | 15.19 | 1.73 | 5.46 | |
| Peters | 17.67 | 1.93 | 5.12 | |

Fresh Pollen Germination:

'Tejon' pollen germination at pollen shed was high and significantly higher than 'Randy' or 'Peters' (Table 2A, Table 2B, FIG. 1). 'Tejon' pollen germination was also compared to male pistachio varieties 'B15-43' (not patented), 'B16-58' (not patented), and 'B19-69' (also known as 'Famoso'). 'Randy' has produced large quantities of viable pollen in prior tests and the current results may reflect differences in flower maturity when 'Randy' was collected (e.g. mid bloom vs. later flowering).

TABLE 2A

Least Squares Means for germination of fresh pollen in Year 15, counted immediately after flowering.

| a) Cultivar | Mean % | SE Mean % |
|---|---|---|
| Tejon | 85.09 | 2.334 |
| Peters | 66.67 | 3.301 |
| Randy | 58.09 | 2.557 |
| B15-43 | 86.19 | 2.334 |
| B16-58 | 90.40 | 2.334 |
| B19-69 | 85.66 | 1.906 |

TABLE 2B

GLM ANOVA showing highly significant differences among cultivars.
GLM Analysis of Variance for Germination of Fresh Pollen

| Source | DF | SS | MS | F | P |
|---|---|---|---|---|---|
| Cultivar | 5 | 0.84564 | 0.16913 | 25.87 | 0.000 |
| Error | 64 | 0.41841 | 0.00654 | | |
| Total | 69 | 1.26405 | | | |

S = 0.0808560
R-Sq = 66.90%
R-Sq(adj) = 64.31%

Figure 2:
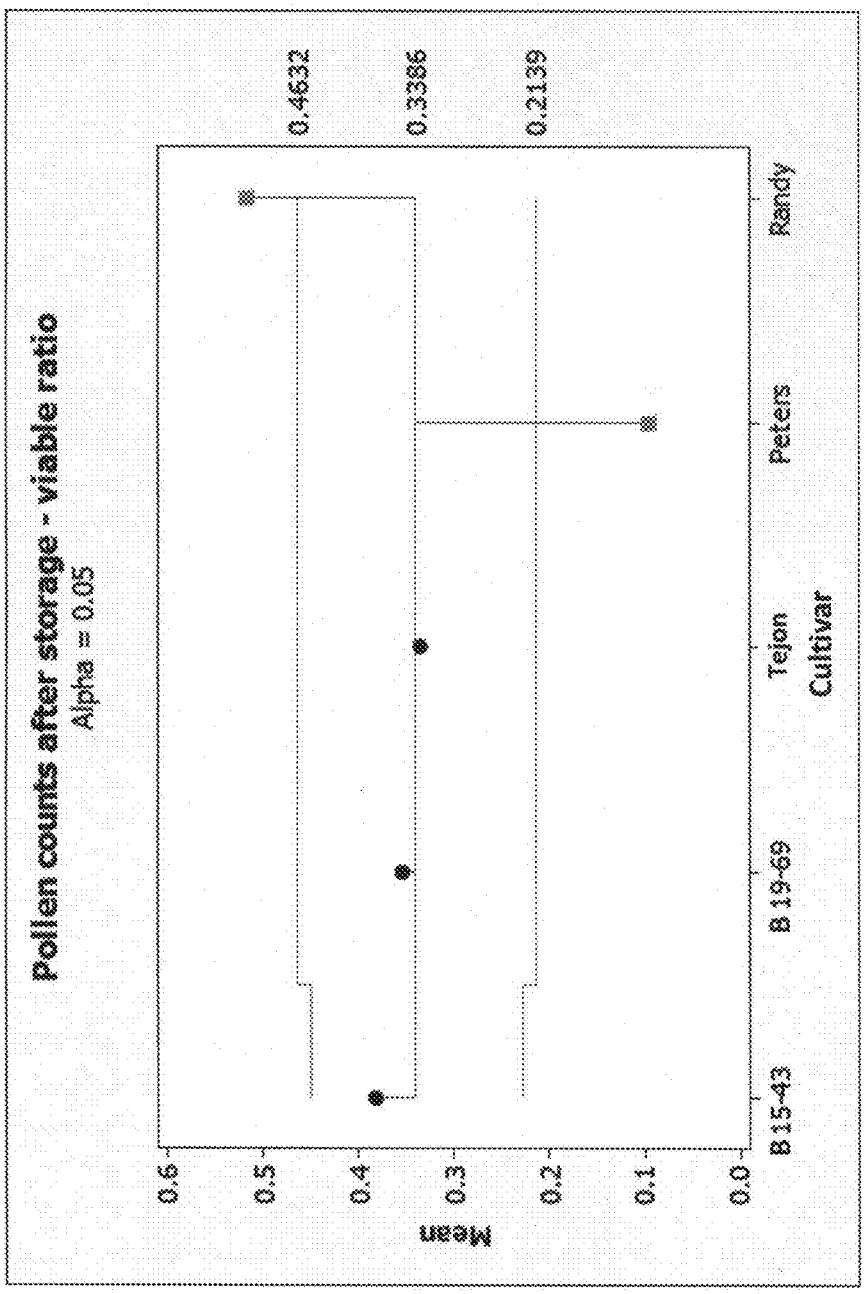
FIG. 2 illustrates the mean germination ratio of stored pollen for 7-year-old 'Tejon' trees and other male pistachio varieties in Year 15. Shown is the analysis of means (MiniTab 17) with 5% SD, where a value of 1.0=100%.

Pollen Viability After Storage:

A second set of pollen counts was done after the pollen was stored desiccated at 4° C. for 3 to 4 days (Table 3A, Table 3B, FIG. 2). 'Randy' pollen was significantly more durable than other male varieties, and 'Peters' pollen was less durable than the other males. 'Tejon' was intermediate in pollen germination after 4 days in storage. In prior tests of many males, both 'Peters' and 'Randy' had better cold-storage durability than most other males evaluated. The overall evaluation of 'Tejon' showed that pollen viability was good and sufficient, even in the low-chill Year 15 (Table 4A), to provide sufficient pollination for females with which it has a flowering period overlap.

TABLE 3A

Least Squares Means for germination of pollen in Year 15, counted after 4° C. storage.

| Cultivar | Mean % | SE Mean % |
|---|---|---|
| Tejon | 33.60 | 4.915 |
| Peters | 9.40 | 4.915 |
| Randy | 51.73 | 4.915 |
| B15-43 | 38.20 | 4.487 |
| B19-69 | 35.48 | 4.915 |

TABLE 3B

GLM ANOVA showing highly significant differences among cultivars. GLM Analysis of Variance for Germination of Stored Pollen

| Source | DF | SS | MS | F | P |
|---|---|---|---|---|---|
| Cultivar | 4 | 0.47137 | 0.11784 | 9.76 | 0.000 |
| Error | 21 | 0.25368 | 0.01208 | | |
| Total | 25 | 0.72504 | | | |

S = 0.109908
R-Sq = 65.01%
R-Sq(adj) = 58.35%

Figure 3:
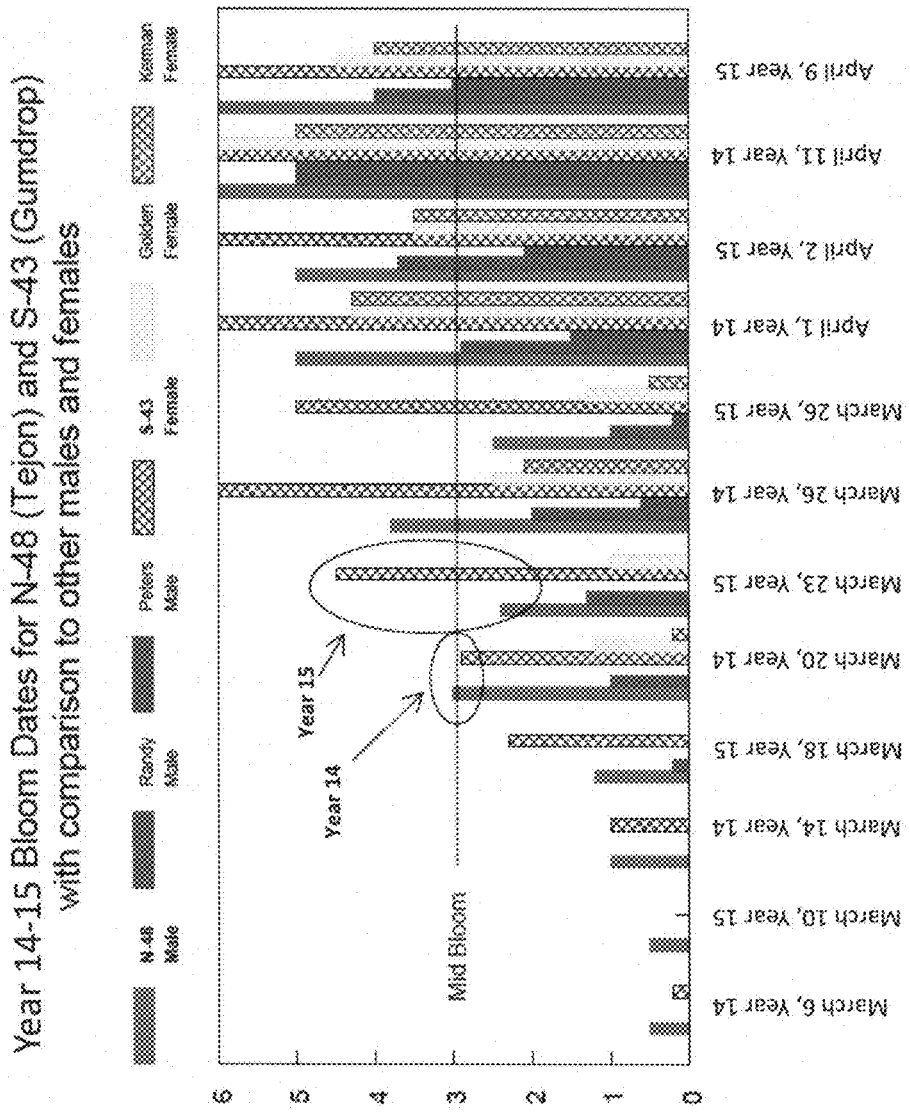
FIG. 3 illustrates bloom dates for Years 14-15 for 2- to 3-year-old 'Tejon' trees and 'Gumdrop' compared to several commercial male and female pistachio varieties. Y-axis shows bloom rating on a scale of 0 to 6 as follows: 0=dormant buds, 1=green tip on flower bud, 2=> (greater than) five open buds on tree, 3=mid bloom, 4=full bloom, 5=late bloom, 6=bloom finished.

Flowering Dates:

Flowering was evaluated on the whole tree using a visual scale from 0 to 6, where 0=dormant buds, 1=green tip on flower bud, 2=greater than five open buds on tree, 3=mid bloom, 4=full bloom, 5=late bloom, 6=bloom finished. These scores are averages, since there are differences both within and between trees due to variables such as, for example, the amount of sun exposure, the location of the trees in the orchard, the location of the orchard, etc. Scores of 3 to 4 provide the most viable pollen for the female trees. Table 4A shows flowering dates for several males and their relationship to female cultivars. Years 14 and 15 were low chill years and both 'Randy' and 'Peters' were delayed relative to 'Kerman'. Usually, 'Peters' is approximately coincident with 'Kerman', although 'Peters' generally has somewhat later flowering relative to 'Kerman', especially in low-chill years. In Year 15, 'Randy' actually overlapped with both 'Kerman' and 'Golden Hills', although 'Randy' was developed as a pollinizer for 'Golden Hills' which is usually earlier than 'Kerman' (FIG. 3). 'Tejon' had good flowering overlap with 'Gumdrop', while no other male variety was early enough to pollinize 'Gumdrop'.

In the low chill years of Year 14 and Year 15, both 'Peters' and 'Randy' flowered six days later than their female counterparts 'Kerman' and Golden Hills. However, 'Tejon' and 'Gumdrop' remained more closely synchronized. 'Tejon' is thus a suitable pollinizer for the early flowering female variety 'Gumdrop'.

TABLE 4A

Bloom maturity evaluation scores by date for Years 14 and 15.

| Cultivar Year 14 | | Evaluation Date: March 6, Year 14 | March 14, Year 14 | March 20, Year 14 |
|---|---|---|---|---|
| Tejon | Male | 0.5 | 1 | 3.0 |
| Randy | Male | 0 | 0 | 1.0 |
| Peters | Male | 0 | 0 | 0.0 |
| Gumdrop | Female | 0.2 | 1 | 2.9 |
| Golden Hills | Female | 0 | 0 | 1.2 |
| Kerman | Female | 0 | 0 | 0.2 |

| Cultivar Year 14 | | Evaluation Date: March 26, Year 14 | April 1, Year 14 | April 11, Year 14 |
|---|---|---|---|---|
| Tejon | Male | 3.8 | 5 | 6 |
| Randy | Male | 2 | 2.9 | 5 |
| Peters | Male | 0.6 | 1.5 | 4 |
| Gumdrop | Female | 6 | 6 | 6 |
| Golden Hills | Female | 2.5 | 4.3 | 6 |
| Kerman | Female | 2.1 | 3 | 5 |

| Year 15 | | Evaluation Date: March 10, Year 15 | March 18, Year 15 | March 23, Year 15 |
|---|---|---|---|---|
| Tejon | Male | 0.5 | 1.2 | 2.4 |
| Randy | Male | 0 | 0.2 | 1.3 |
| Peters | Male | 0 | 0 | 0 |
| Gumdrop | Female | 0 | 2.3 | 4.5 |
| Golden Hills | Female | 0 | 0 | 1 |
| Kerman | Female | 0 | 0 | 0 |

| Year 15 | | Evaluation Date: March 26, Year 15 | April 2, Year 15 | April 9, Year 15 |
|---|---|---|---|---|
| Tejon | Male | 2.5 | 5 | 6 |
| Randy | Male | 1 | 3.7 | 4 |
| Peters | Male | 0.2 | 2.1 | 3 |
| Gumdrop | Female | 5 | 6 | 6 |
| Golden Hills | Female | 1.3 | 3.5 | 4.5 |
| Kerman | Female | 0.5 | 3.5 | 4 |

Bloom ratings 0 to 6:
0 = dormant buds, 1 = green tip on flower bud, 2 => 5 open buds on tree, 3 = mid bloom, 4 = full bloom, 5 = late bloom, 6 = bloom finished
Note mid-bloom (3)/full bloom (4) dates overlap.

Table 4B shows full bloom dates for 'Peters', 'Randy', 'Tejon', and 'Kerman' at the Jasmine Trial for Years 14 to 17. Year 14 and Year 15 were very low chill years, and bloom was highly variable and erratic across the tree. 'Tejon' trees were 2 years old in Year 14.

TABLE 4B

Jasmine trial full bloom dates for Years 14-17

| Cultivar | Full Bloom Dates: Year 14 | Year 15 | Year 16 | Year 17 |
|---|---|---|---|---|
| Peters (male) | 14-Apr | no bloom | 5-Apr | 12-Apr |
| Randy (male) | 3-Apr | 1-Apr | 22-Mar | 6-Apr |
| Tejon (male) | 26-Mar | 24-Mar | 18-Mar | 31-Mar |
| Kerman (female) | 9-Apr | no bloom | 31-Mar | 14-Apr |

Table 4C shows full bloom timing for 'Kerman', 'Golden Hills', and 'Gumdrop' in the Buttonwillow plot for Years 14 to 17. Bloom was erratic and varied across the tree in Year 14 and Year 15 due to low chill. 'Tejon' trees were 2 years old in Year 14.

TABLE 4C

Buttonwillow trial full bloom dates for Years 14-17

| Cultivar | Full Bloom Dates | | | |
|---|---|---|---|---|
| | Year 14 | Year 15 | Year 16 | Year 17 |
| Peters (male) | 11-Apr | 13-Apr | 31-Mar | 11-Apr |
| Randy (male) | 5-Apr | 9-Apr | 24-Mar | 5-Apr |
| Tejon (male) | 29-Mar | 31-Mar | 20-Mar | 30-Mar |
| Golden Hills (female) | 30-Mar | 1-Apr | 25-Mar | 5-Apr |
| Gumdrop (fesmale) | 25-Mar | 22-Mar | 21-Mar | 28-Mar |
| Kerman (female) | 5-Apr | 9-Apr | 31-Mar | 9-Apr |

Plant Winter Hardiness, Heat Tolerance, and Drought Tolerance:

'Tejon', as is typical of *Pistacia vera* L., will tolerate temperatures greater than −5° C. to −10° C. The rootstock on which it is grafted, however, can sustain significant damage at −5° C. after a few hours. The 'Tejon' cultivar is typically grown in a hot dry environment, and has been grown in a location having typical summer temperatures greater than 40° C. to 42° C. All California pistachio cultivars are grown as an irrigated crop and require about 1000 mm of water during the growing season. Pistachio cultivars will tolerate poor quality water and do not show significant yield loss or damage up to EC (electrical conductivity) 8-12.

Figure 4:
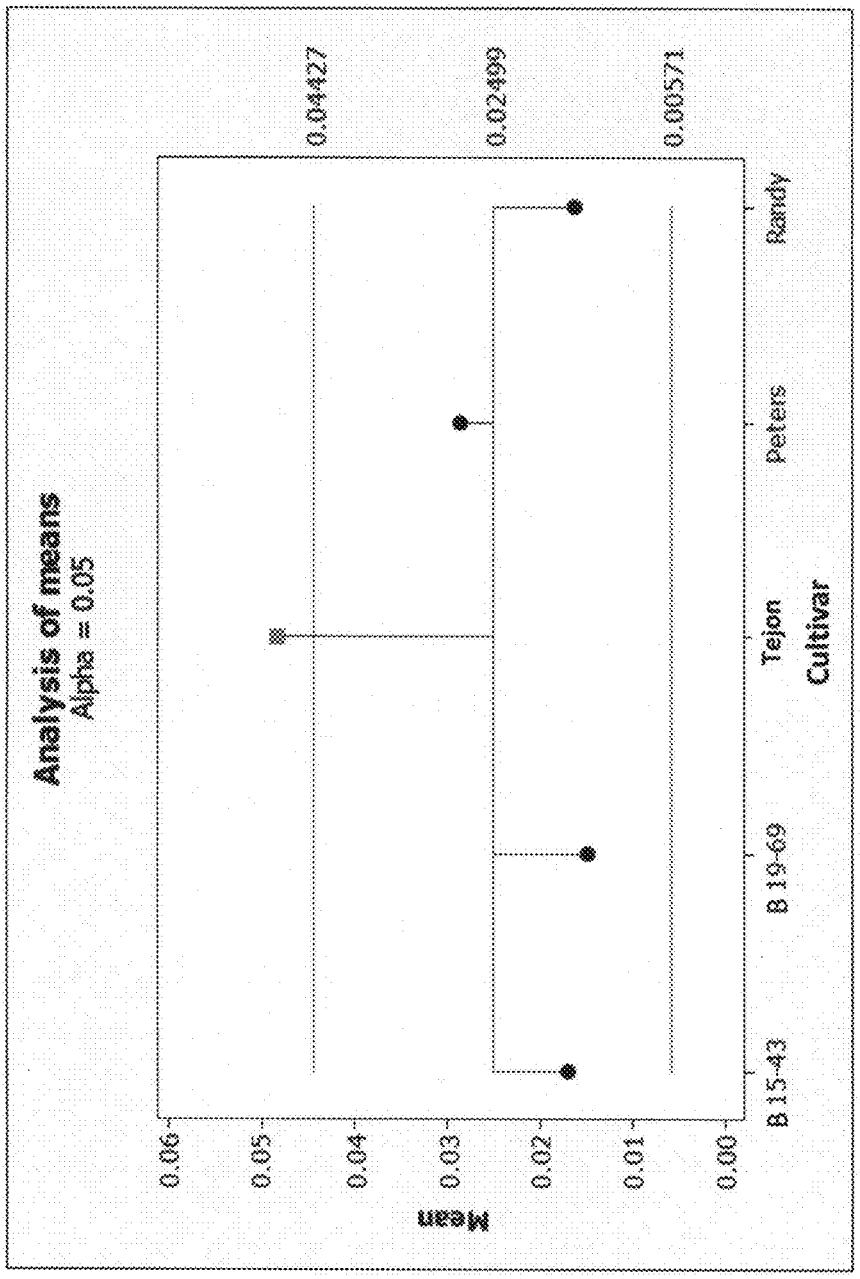
FIG. 4 illustrates the mean pollen weight per inflorescence (grams) for 7-year-old 'Tejon' trees and other male pistachio varieties in Year 15. Shown is the analysis of means (MiniTab 17) with 5% SD.

Pollen Quantities:

During March of Year 15 (7-year-old 'Tejon' trees), branches with dehiscing inflorescences were collected and evaluated from the Bakersfield trial. Treatments involved taking four to five shoots that were 8-12 inches long with dehiscing inflorescences and placing them on craft paper overnight, followed by pollen collection the following morning. Pollen from three replicates of each treatment were collected and weighed. Treatments were normalized by counting the number of actively dehiscing inflorescences. ANOVA and ANOMA were performed with MiniTab 17. 'Tejon' proved, by comparison to other existing male cultivars, to have good quantities of pollen available for pollination (Table 5A, Table 5B, and FIG. 4).

TABLE 5A

Least Squares Means for pollen quantities (grams/inflorescence).

| Accession | Mean | SE Mean |
|---|---|---|
| Tejon | 0.04833 | 0.007042 |
| Peters | 0.02863 | 0.007042 |
| Randy | 0.01627 | 0.007042 |
| B15-43 | 0.01683 | 0.007042 |
| B19-69 | 0.01487 | 0.007042 |

TABLE 5B

GLM ANOVA for pollen quantities per inflorescence.
GLM for pollen quantification

| Source | DF | SS | MS | F | P |
|---|---|---|---|---|---|
| Cultivar | 4 | 0.002410 | 0.000602 | 4.05 | 0.033 |
| Error | 10 | 0.001488 | 0.000149 | | |
| Total | 14 | 0.003898 | | | |

S = 0.01220
R-Sq = 61.83%
R-Sq(adj) = 46.56%

Figure 8:
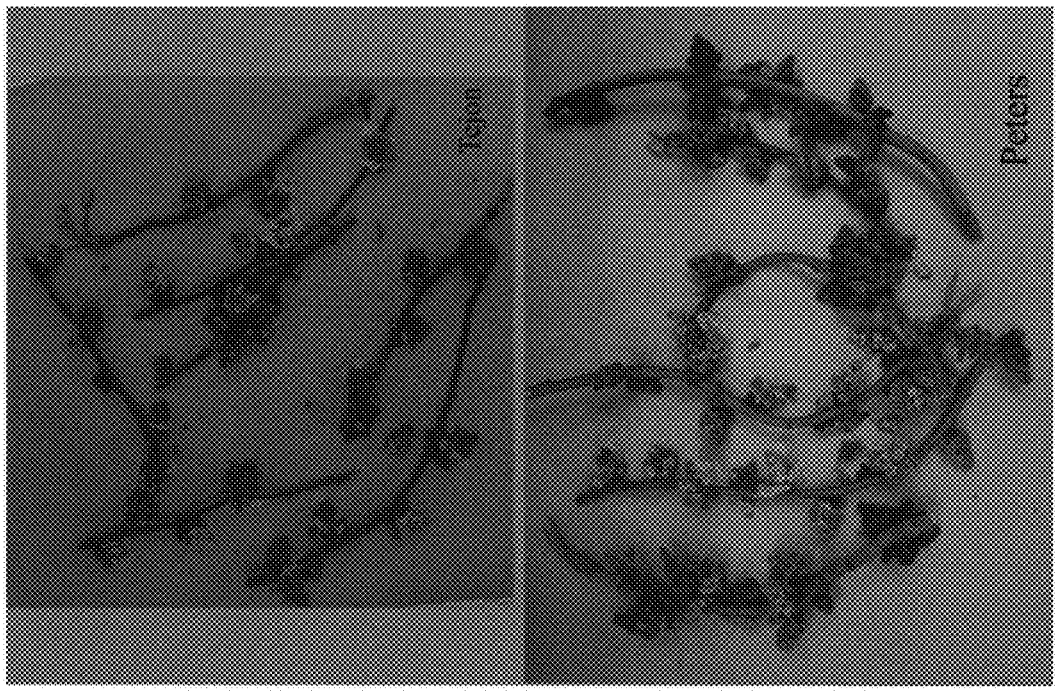
FIG. 8 illustrates a comparison of inflorescences between 5-year-old 'Tejon' trees and 'Peters'.

Inflorescences:

'Tejon' inflorescences are borne laterally on branches, rarely as terminal buds. They are located on one year old wood. The flower buds form a branched compound inflorescence as a compact compressed panicle. The panicles are 2 to 5 cm long when fully expanded and shedding pollen with considerable variation in size. Flower development is from base to tip of the panicle and typically spans several weeks, depending on weather conditions during individual seasons. 'Tejon' inflorescences are green to light green (136B-139B) similar to 'Peters' inflorescences which are distinctly green (136B-139B) (FIG. 8). Both cultivars have some inflorescences with a reddish tinge (42C-43C). Individual flowers are 1-2 mm in diameter. 'Tejon' is a male pistachio tree, which means that all flowers are male. Because there are no female flowers, no seed is produced. Tips and outside of individual flowers are pinkish red (48C, 49D) changing to yellow (154B-D), and flowers near the base of the panicles are tinged red (42C-43C) prior to opening of individual flowers. Flowers do not have petals and have 5-6 stamens each with 4 lobes (J. I. Hormaza et al. (1996) Amer. J. Botany 83:759-766). Pollen is shed from the terminal ends of the stamens.

Figure 5A:
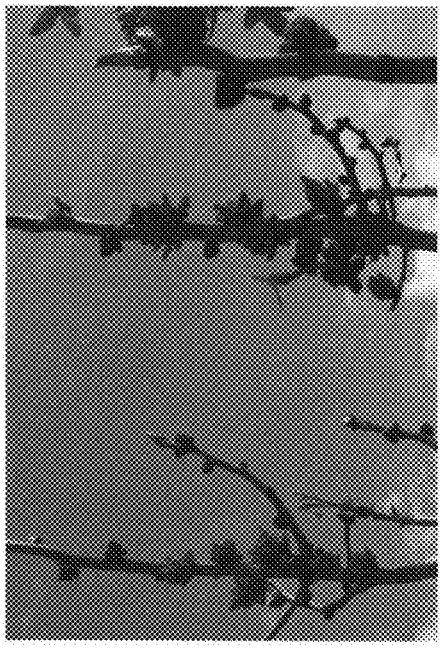
FIG. 5A-FIG. 5B illustrates a comparison of inflorescence density for 3-year-old 'Tejon' trees (FIG. 5A) and 'Peters' (FIG. 5B).
Figure 5B:
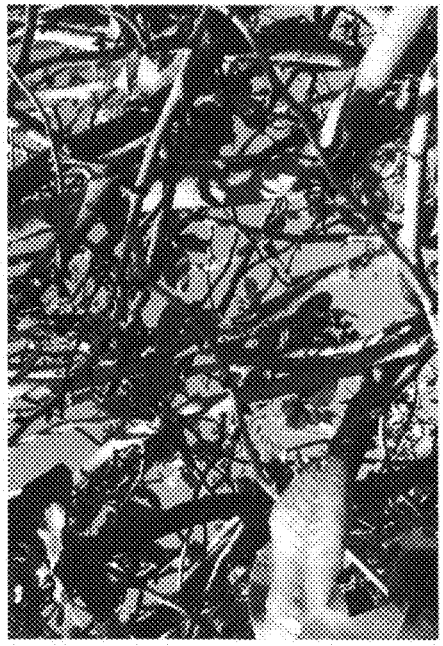
Figure 6:
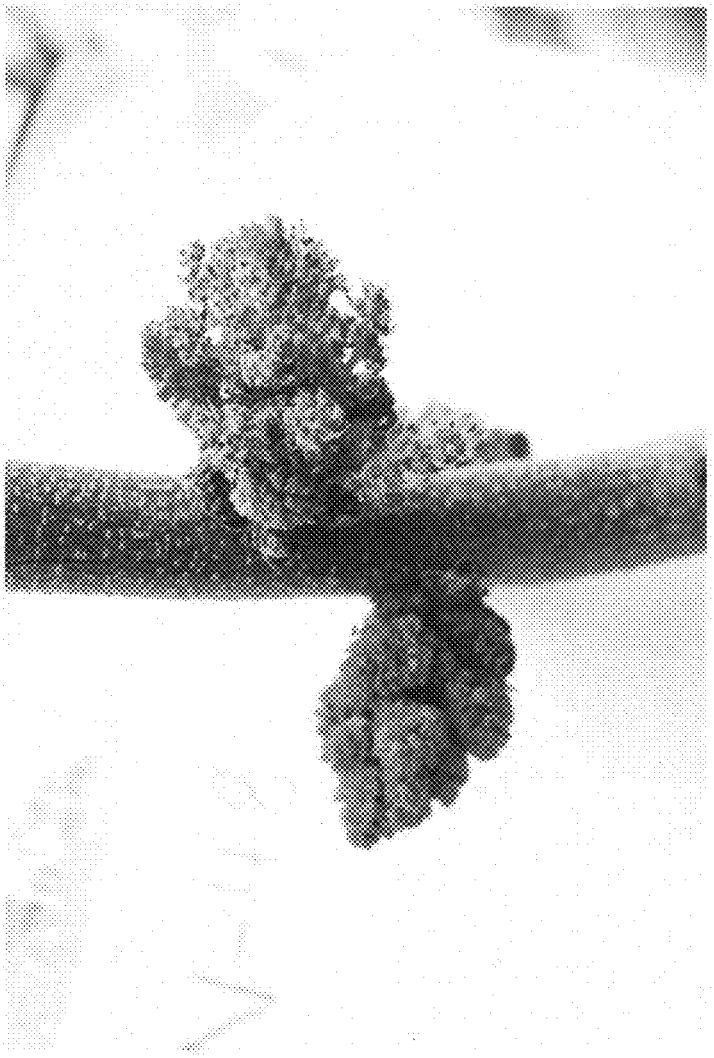
FIG. 6 illustrates the dehiscing inflorescences of 3-year-old 'Tejon' trees.

Inflorescence Density:

The tree canopies of several male cultivars were photographed to provide an approximate evaluation of the number of inflorescences in the canopy. It is difficult to develop methods that accurately quantify this variable, which is highly dependent on tree size, pruning, and tree health. FIG. 5A and FIG. 5B provide a visual comparison of 'Tejon' and 'Peters', taken at their respective bloom periods. 'Peters' had very scattered bloom in Year 15, with many buds never breaking dormancy. An image of the dehiscing inflorescences of 'Tejon' is provided in FIG. 6.

Figure 7:
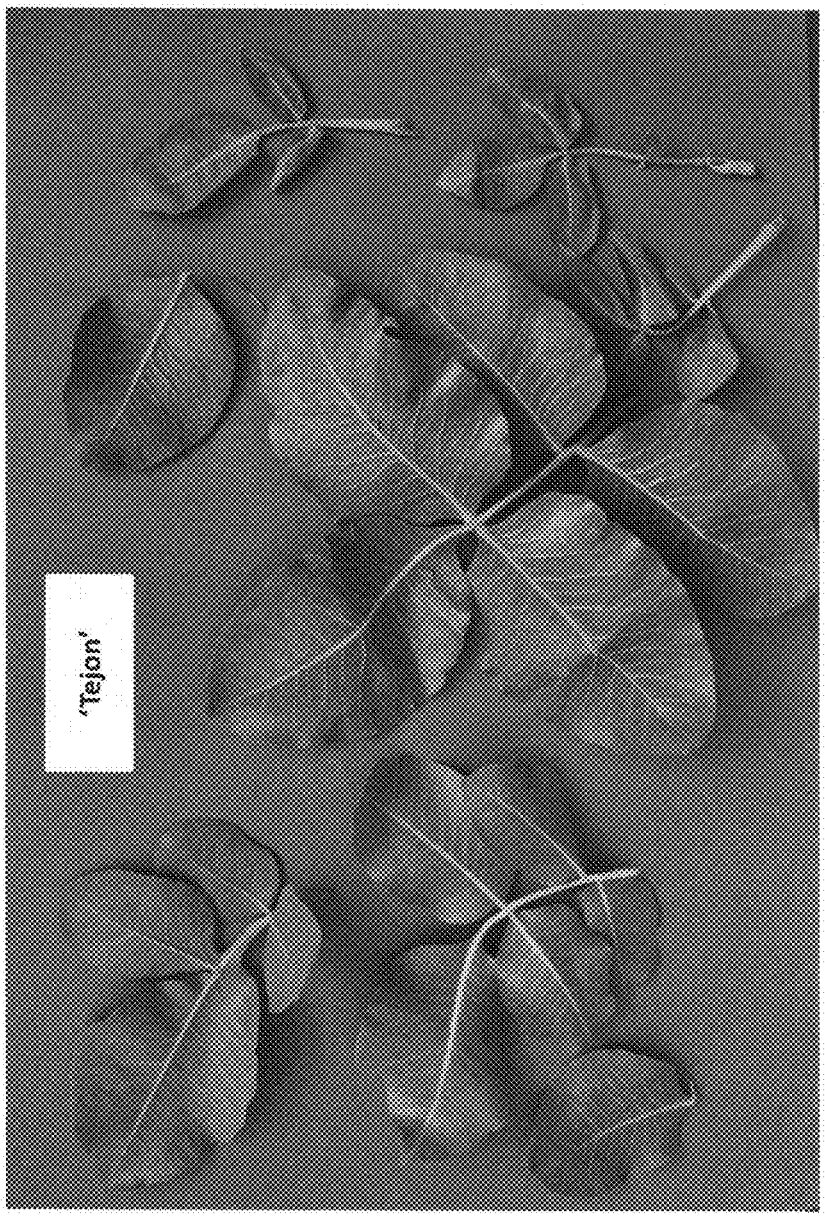
FIG. 7 illustrates the leaves of 3-year-old 'Tejon' trees.
Figure 9:
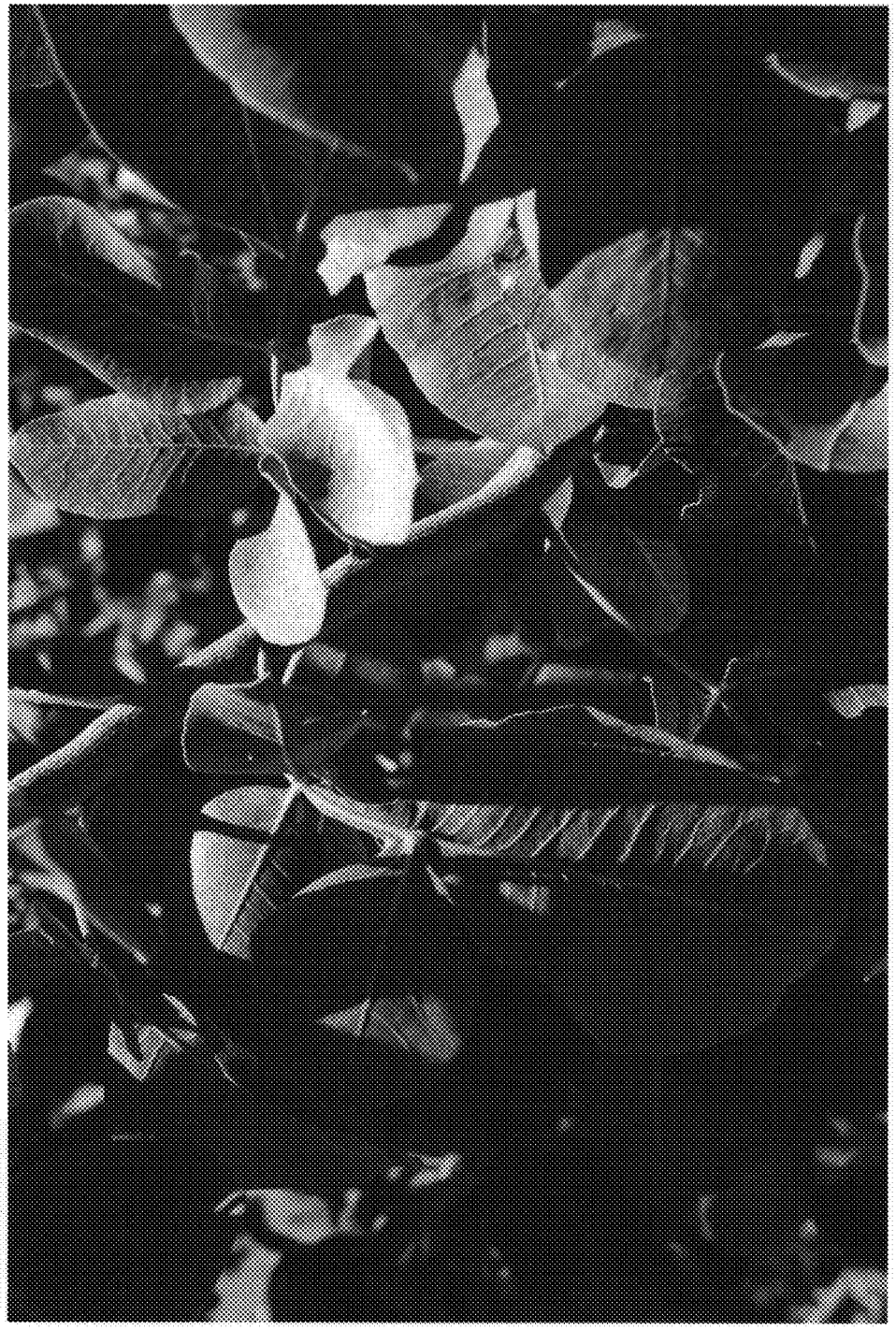
FIG. 9 illustrates the venation pattern on the leaves of 5-year-old 'Tejon' trees.

Leaves:

'Tejon' leaves are highly variable in the details of their form, shape and size within the tree. In general the leaves are deciduous simple compound imparipinnate with one or two pairs of oppositely arranged lateral leaflets. However, the leaves can also be trifoliate and on branches with an abundance of new vegetative growth only one or no lateral leaflets may be present. Leaflet margins are entire to slightly crenate. Leaf and leaflet sizes are highly variable. Petioles may be 30 mm to more than 60 mm to the first lateral. The petiole diameter is approximately 1-2 mm, and therefore too small to be measured accurately. Leaflets are oval to ovate and 5-8 cm long. Terminal leaflets can be less than 8 cm to greater than 16 cm. Leaflets vary considerably in shape, in general being ovate with cuspidate to rounded apex and rounded base (FIG. 7). Margins of leaf blades are entire. Leaf surfaces are glabrous, smooth, and waxy. Leaf venation is of the cladodromous type as described by Hickey (1973) Amer. J. Botany 60:17-33 and as shown in FIG. 9. Typical petiole/leaf values are shown in Table 6 (15 observations) for Year 17 data (5-year-old 'Tejon' trees) from the Jasmine trial. Differences were tested at 5% level for both petiole and terminal leaflets. 'Randy' has shorter petioles than 'Tejon' or 'Peters' (p=0.032), while 'Tejon' was intermediate to 'Randy' and 'Peters'. Terminal leaflet length was also significant (p=0.023) with 'Tejon' being significantly larger than 'Randy' (Tukey test 5%).

TABLE 6

Typical petiole/leaf values

| Cultivar | Variable | Mean | SD | p-value |
|---|---|---|---|---|
| Tejon | petiole length (cm) | 5.28 | 1.09 | 0.032 |
| Randy | petiole length (cm) | 4.77 | 0.96 | |
| Peters | petiole length (cm) | 5.98 | 1.54 | |
| Tejon | terminal leaflet (cm) | 10.37 | 1.74 | 0.023 |
| Randy | terminal leaflet (cm) | 8.64 | 1.46 | |
| Peters | terminal leaflet (cm) | 9.33 | 1.75 | |

For leaves, color evaluations were done on 'Tejon' and 'Randy' (as a comparison) leaves collected during the summer of Year 14 (2-year-old 'Tejon' trees). The results are presented in Table 7 below. Images of the leaves of 'Tejon' are presented in FIG. 7 and FIG. 9.

TABLE 7

Leaf color evaluation for 'Tejon' and 'Randy'

| Selection | Mature Leaf - Top | Mature Leaf - Bottom | New Leaf - Top | New Leaf - Bottom | Midrib/ Petiole |
|---|---|---|---|---|---|
| 'Randy' | 136A, 136B green | 135B green | 137C green | 137D green | 141D, 143D pale green |

TABLE 7-continued

Leaf color evaluation for 'Tejon' and 'Randy'

| Selection | Mature Leaf - Top | Mature Leaf - Bottom | New Leaf - Top | New Leaf - Bottom | Midrib/ Petiole |
|---|---|---|---|---|---|
| 'Tejon' ('N-48') | 136C green | 139B green | 139C green | 139D green | 143D pale green |

Response to Pests and/or Diseases:

'Tejon' has not been specifically evaluated for resistance or susceptibility to pistachio diseases. This variety is grown in a location where typical pistachio diseases are minimal and which is managed to minimize disease development. It is expected that susceptibility to *Botryosphaeria dothidea, Botrytis cinerea*, or *Alternaria alternata* would be similar to other commercial pistachio cultivars since *Pistacia vera* L. in California is generally susceptible to these diseases. Most pistachio insect pests are controlled with insecticides, which have been used where 'Tejon' is grown. Significant differences in unspecified insect damage were not found among the tested cultivars, including 'Tejon'.

What is claimed is:

1. A new and distinct variety of pistachio tree designated 'Tejon' as shown and described herein.

* * * * *